US012564368B2

(12) United States Patent
Miyahara

(10) Patent No.: US 12,564,368 B2
(45) Date of Patent: Mar. 3, 2026

(54) NUCLEAR MEDICINE DIAGNOSIS APPARATUS, ACQUISITION PERIOD EXTENDING METHOD, AND NON-TRANSITORY COMPUTER-READABLE MEDIUM

(71) Applicant: CANON MEDICAL SYSTEMS CORPORATION, Otawara (JP)

(72) Inventor: Masaki Miyahara, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 18/596,841

(22) Filed: Mar. 6, 2024

(65) Prior Publication Data

US 2024/0298993 A1      Sep. 12, 2024

(30) Foreign Application Priority Data

Mar. 9, 2023      (JP) ................................. 2023-036506

(51) Int. Cl.
    *A61B 6/00*        (2024.01)
    *A61B 6/03*        (2006.01)
    *A61B 6/04*        (2006.01)
    *G06T 11/00*       (2006.01)
(52) U.S. Cl.
    CPC ............. *A61B 6/541* (2013.01); *A61B 6/037* (2013.01); *G06T 11/005* (2013.01); *A61B 6/0407* (2013.01)

(58) Field of Classification Search
    CPC ....... A61B 6/5264; A61B 6/037; A61B 6/541; G06T 11/005
    See application file for complete search history.

(56) References Cited

U.S. PATENT DOCUMENTS

| | | | | |
|---|---|---|---|---|
| 2003/0065315 A1* | 4/2003 | Hareyama | .............. | A61B 90/30 |
| | | | | 606/18 |
| 2015/0272481 A1* | 10/2015 | Glaser | .................... | G16H 40/67 |
| | | | | 600/595 |
| 2016/0354047 A1* | 12/2016 | Huston | ................ | A61B 6/5288 |
| 2017/0039734 A1* | 2/2017 | Langan | .................. | A61B 6/025 |
| 2017/0042492 A1 | 2/2017 | Noshi | | |
| 2019/0192104 A1* | 6/2019 | Thran | .................... | A61B 5/352 |
| 2021/0196219 A1* | 7/2021 | Jansen | .................. | G06T 11/008 |
| 2022/0005240 A1* | 1/2022 | Shinoda | ................. | A61B 5/004 |
| 2022/0117486 A1* | 4/2022 | Yoshida | ................. | A61B 3/102 |
| 2023/0263478 A1* | 8/2023 | Addison | .............. | A61B 5/1495 |
| | | | | 600/364 |

FOREIGN PATENT DOCUMENTS

JP        2017-37037 A        2/2017

* cited by examiner

*Primary Examiner* — John D Li
(74) *Attorney, Agent, or Firm* — Oblon, McClelland, Maier & Neustadt, L.L.P.

(57)                ABSTRACT
A nuclear medicine diagnosis apparatus according to an embodiment includes processing circuitry. The processing circuitry is configured: to acquire nuclear medicine data by scanning an examined subject; to specify timing of a body movement of the examined subject during the acquisition of the nuclear medicine data; and to extend an acquisition period of the scan on the basis of the timing.

7 Claims, 4 Drawing Sheets

NUCLEAR MEDICINE DIAGNOSIS APPARATUS, ACQUISITION PERIOD EXTENDING METHOD, AND NON-TRANSITORY COMPUTER-READABLE MEDIUM

CROSS-REFERENCE TO RELATED APPLICATIONS

This application is based upon and claims the benefit of priority from Japanese Patent Application No. 2023-036506, filed on Mar. 9, 2023; the entire contents of which are incorporated herein by reference.

FIELD

Embodiments described herein relate generally to a nuclear medicine diagnosis apparatus, an acquisition period extending method, and a non-transitory computer-readable medium.

BACKGROUND

Conventionally, nuclear medicine diagnosis apparatuses such as Positron Emission Tomography (PET) apparatuses are configured to image an examined subject according to an acquisition period set in advance.

Nuclear medicine diagnosis apparatuses have relatively long acquisition periods such as approximately 3 minutes for acquiring data from the abdomen and approximately 10 minutes for acquiring data from the head.

However, when a trouble occurred during an acquisition period, nuclear medicine diagnosis apparatuses are not able to acquire data sufficiently. Further, because the acquired data is insufficient, those nuclear medicine diagnosis apparatuses would unfortunately reconstruct images having degraded quality.

DETAILED DESCRIPTION

Figure 1:
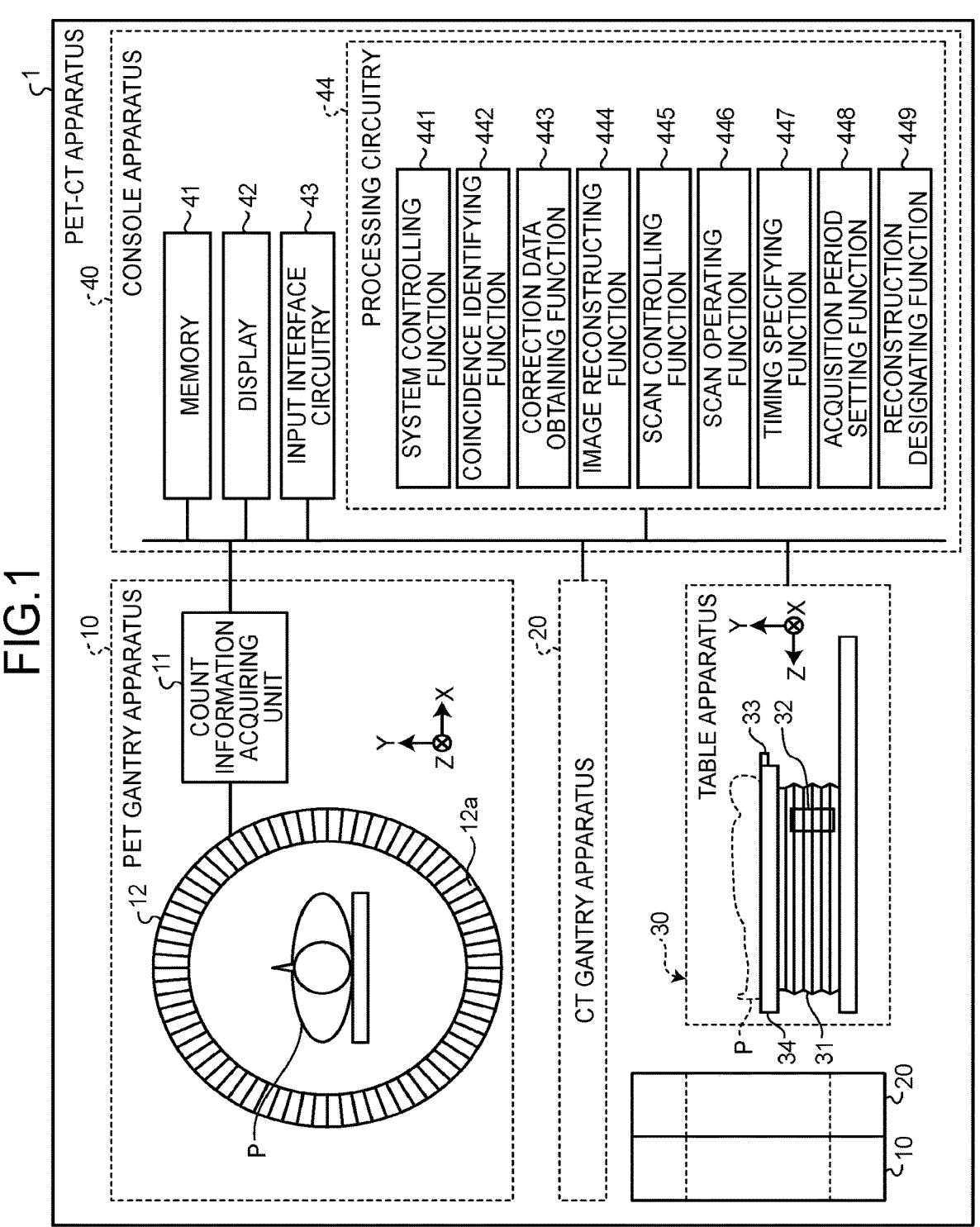
FIG. 1 is a diagram illustrating an exemplary configuration of a PET-Computed Tomography (CT) apparatus according to an embodiment of the present disclosure.

A nuclear medicine diagnosis apparatus according to an embodiment includes processing circuitry. The processing circuitry is configured to acquire nuclear medicine data by scanning an examined subject; to specify timing of a body movement of the examined subject during the acquisition of the nuclear medicine data; and to extend an acquisition period of the scan on the basis of the timing.

Exemplary embodiments of a nuclear medicine diagnosis apparatus, an acquisition period extending method, and a non-transitory computer-readable medium of the present disclosure will be explained below with reference to the accompanying drawings. In the following embodiments, some of the constituent elements referred to by using mutually the same reference characters are assumed to perform the same or similar operations, and duplicate explanations thereof will be omitted as appropriate.

Further, to explain specific examples, the nuclear medicine diagnosis apparatuses of the present embodiments are each assumed to be a Positron Emission Tomography-Computed Tomography (PET-CT) apparatus. However, the nuclear medicine diagnosis apparatuses do not need to be PET-CT apparatuses and may be PET apparatuses. Alternatively, the nuclear medicine diagnosis apparatuses may be Single Photon Emission Computed Tomography (SPECT) apparatus.

Embodiments of the Present Disclosure

FIG. 1 is a diagram illustrating an exemplary configuration of a PET-CT apparatus 1 according to an embodiment of the present disclosure. As illustrated in FIG. 1, the PET-CT apparatus 1 includes a PET gantry apparatus 10, a CT gantry apparatus 20, a table apparatus 30, and a console apparatus 40.

In the present embodiment, the central axis of a PET detector 12 or the longitudinal direction of a tabletop 33 of the table apparatus 30 is defined as a Z-axis direction; the axial direction orthogonal to the Z-axis direction and parallel to a floor surface is defined as an X-axis direction; and the axial direction orthogonal to the Z-axis direction and perpendicular to the floor surface is defined as a Y-axis direction. Although FIG. 1 depicts the PET gantry apparatus 10 and the CT gantry apparatus 20 in multiple locations for the sake of convenience in the explanations, the actual PET-CT apparatus 1 includes one PET gantry apparatus 10 and one CT gantry apparatus 20.

The PET gantry apparatus 10 includes a count information acquiring unit 11 and a PET detector 12. The PET detector 12 is configured to detect gamma rays (pair annihilation gamma rays) released from the inside of an examined subject (hereinafter, "patient") P. The PET detector 12 is a detector in which a plurality of PET detector modules 12a are arranged in a ring formation so as to surround the patient P.

The PET detector modules 12a are each configured to scintillate and emit light, in response to the gamma rays released from the inside of the patient P. The PET detector modules 12a are configured to detect the emitted light and to convert the detected light into electrical signals corresponding to energy thereof.

The count information acquiring unit 11 is configured to generate count information from output signals of the PET detector modules 12a. Further, the count information acquiring unit 11 is configured to store the generated count information into a memory 41. For example, the count information acquiring unit 11 is realized by using a processor. For example, the count information acquiring unit 11 is configured to acquire the count information by generating the count information from the output signals of the PET detector modules 12a. The count information includes detection positions of the gamma rays, energy values, and detection times. Further, the count information acquiring unit 11 is configured to transmit, to the console apparatus 40, the count information in a data format called single list mode data, which is data before coincidence is identified.

More specifically, the count information acquiring unit 11 is configured to identify light emission positions (scintillation positions) of the gamma rays in scintillators. When scintillator pixels and optical sensors are linked in one-to-one correspondence, the count information acquiring unit 11 is configured to specify each of the light emission positions by specifying a scintillator pixel corresponding to the optical sensor that output a pulse. In another example, when a small number of optical sensors are kept in correspondence with a large number of scintillator pixels, the count information acquiring unit 11 may estimate the light emission positions by performing a center-of-gravity calculation on the outputs of the small number of optical sensors.

The count information acquiring unit 11 is configured to estimate energy from the output pulses output by the optical sensors. The count information acquiring unit 11 is configured to estimate the energy by using an energy integration scheme in which the energy integral is calculated of a range where the output pulse exceeds a prescribed threshold value, so as to obtain the energy through a conversion process. Alternatively, the count information acquiring unit 11 may estimate the energy by using a Time-over-Threshold (TOT) scheme in which a time range where the output pulse exceeds a prescribed threshold value is converted into the energy. The count information acquiring unit 11 is configured to specify timing at which the output pulse output by the optical sensor exceeds the threshold value as the detection times.

The CT gantry apparatus 20 is an apparatus including an imaging system configured to emit X-rays onto the patient P and to acquire detection data of X-rays that have passed through the patient P. The CT gantry apparatus 20 is configured to obtain the detection data for generating correction-purpose data (an attenuation map or a u-map) to be used at the time of reconstructing a PET image.

The table apparatus 30 is an apparatus on which the patient P to be scanned is placed and moved and includes a base 31, a table driving apparatus 32, the tabletop 33, and a tabletop supporting frame 34. The base 31 is a casing configured to support the tabletop supporting frame 34 so as to be movable in vertical directions. The table driving apparatus 32 is a motor or an actuator configured to move the tabletop 33 on which the patient P is placed, in the long-axis directions of the tabletop 33. The table driving apparatus 32 is configured to move the tabletop 33, according to control exercised by the console apparatus 40, control exercised by the PET gantry apparatus 10, and control exercised by the CT gantry apparatus 20. The tabletop 33 provided on the top face of the tabletop supporting frame 34 is a board on which the patient P is placed. In addition to the tabletop 33, the table driving apparatus 32 may move the tabletop supporting frame 34 in the long-axis directions of the tabletop 33.

To scan the patient P, the table apparatus 30 may move the tabletop 33 according to a step-and-shoot scheme by which scanning and moving of the tabletop 33 are alternately performed or may move the tabletop 33 according to a continuous table moving scheme by which the tabletop 33 is moved while a scan is performed.

The console apparatus 40 includes the memory 41, a display 42, an input interface circuitry 43, and processing circuitry 44. Although the console apparatus 40 is described as a separate member from the PET gantry apparatus 10 and the CT gantry apparatus 20, the console apparatus 40 or one or more of the constituent elements of the console apparatus 40 may be included in either the PET gantry apparatus 10 or the CT gantry apparatus 20.

For example, the memory 41 is realized by using a semiconductor memory element such as a Random Access Memory (RAM) or a flash memory, or a hard disk, an optical disk, or the like. For example, the memory 41 is configured to store therein projection data and CT image data. Further, for example, the memory 41 is configured to store therein programs used by circuitry included in the PET-CT apparatus 1 for realizing various types of functions. The memory 41 may be realized by a group of servers (a cloud) connected to the PET-CT apparatus 1 via a network.

The display 42 is configured to display various types of information. For example, the display 42 is configured to output medical images (CT images, PET images) generated by the processing circuitry 44, a Graphical User Interface (GUI) for receiving various types of operations from an operator, and the like. In an example, as the display 42, it is possible to use a Liquid Crystal Display (LCD), an Organic Electroluminescence Display (OELD), a plasma display, or other arbitrary displays, for instance, as appropriate. Further, the display 42 may be provided for the PET gantry apparatus 10 or the CT gantry apparatus 20. Furthermore, the display 42 may be of a desktop type or may be configured with a tablet terminal or the like capable of wirelessly communicating with the console apparatus 40 main body.

The input interface circuitry 43 is configured to receive various types of input operations from the operator, to convert the received input operations into electrical signals, and to output the electrical signals to the processing circuitry 44. For example, the input interface circuitry 43 is configured to receive, from the operator, an acquisition condition used at the time of acquiring projection data, a reconstruction condition used at the time of reconstructing a CT image, an image processing condition used at the time of generating a post-processed image from a CT image, and the like. As the input interface circuitry 43, it is possible to use, for example, a mouse, a keyboard, a trackball, a switch, a button, a joystick, a touchpad, a touch panel display, and/or the like, as appropriate.

In the present embodiment, the input interface circuitry 43 does not necessarily have to include physical operational component parts such as the mouse, the keyboard, the trackball, the switch, the button, the joystick, the touchpad, the touch panel display, and/or the like. For instance, possible examples of the input interface circuitry 43 include electrical signal processing circuitry configured to receive an electrical signal corresponding to an input operation from an external input mechanism provided separately from the apparatus and to output the electrical signal to the processing circuitry 44. Further, the input interface circuitry 43 is an example of an input unit. Furthermore, the input interface circuitry 43 may be provided for the PET gantry apparatus 10 or the CT gantry apparatus 20. Alternatively, the input interface circuitry 43 may be configured by using a tablet terminal or the like capable of wirelessly communicating with the console apparatus 40 main body.

The processing circuitry 44 is configured to control operations of the entirety of the PET-CT apparatus 1. The processing circuitry 44 includes, for example, a system controlling function 441, a coincidence identifying function 442, a correction data obtaining function 443, an image reconstructing function 444, a scan controlling function 445, a scan operating function 446, a timing specifying function 447, an acquisition period setting function 448, and a reconstruction designating function 449. In an embodiment, processing functions performed by the system controlling function 441, the coincidence identifying function 442, the correction data obtaining function 443, the image reconstructing function 444, the scan controlling function 445, the scan operating function 446, the timing specifying function 447, the acquisition period setting function 448, and the reconstruction designating function 449 are stored in the memory 41 in the form of computer-executable programs. The processing circuitry 44 is a processor configured to realize the functions corresponding to the programs by reading and executing the programs from the memory 41. In other words, the processing circuitry 44 that has read the programs has the functions illustrated within the processing circuitry 44 in FIG. 1. The memory 41 is a non-transitory computer-readable medium and is an example of a storage medium storing therein instructions to be executed by a computer.

Although the example was explained with reference to FIG. 1 in which the single piece of processor realizes the system controlling function 441, the coincidence identifying function 442, the correction data obtaining function 443, the image reconstructing function 444, the scan controlling function 445, the scan operating function 446, the timing specifying function 447, the acquisition period setting function 448, and the reconstruction designating function 449, it is also acceptable to structure the processing circuitry 44 by combining together a plurality of independent processors, so that the functions are realized as a result of the processors executing the programs. Further, although the example was explained with reference to FIG. 1 in which a single piece of storage circuitry such as the memory 41 has stored therein the programs corresponding to the processing functions, it is also acceptable to provide a plurality of pieces of storage circuitry in a distributed manner, so that the processing circuitry 44 reads a corresponding program from each of the individual pieces of storage circuitry.

The term "processor" used in the above description denotes, for example, a Central Processing Unit (CPU), a Graphical Processing Unit (GPU), or circuitry such as an Application Specific Integrated Circuit (ASIC) or a programmable logic device (e.g., a Simple Programmable Logic Device (SPLD), a Complex Programmable Logic Device (CPLD), or a Field Programmable Gate Array (FPGA)). One or more processors are configured to realize the functions by reading and executing the programs saved in the memory 41. Alternatively, instead of having the programs saved in the memory 41, it is also acceptable to directly incorporate the programs into the circuitry of the one or more processors. In that situation, the one or more processors are configured to realize the functions by reading and executing the programs incorporated in the circuitry thereof.

The system controlling function 441 is configured to control the various types of functions of the processing circuitry 44 on the basis of the input operations received from the operator via the input interface circuitry 43.

The coincidence identifying function 442 is configured to generate list mode data by identifying coincidence of events in the single list mode data generated by the count information acquiring unit 11. To specify two events detected approximately at the same time, the coincidence identifying function 442 is configured to pair up the events detected within a prescribed time window (a ps order). The coincidence identifying function 442 does not necessarily need to be included in the processing circuitry 44 and may be included in the count information acquiring unit 11. In other words, the count information acquiring unit 11 may transmit the count information in the data format called the list mode data, to the console apparatus 40.

The correction data obtaining function 443 is configured to obtain a CT image as correction data, by obtaining projection data from the CT gantry apparatus 20 and performing a reconstructing process thereon.

The image reconstructing function 444 is configured to generate a PET image by reconstructing the count information generated by the coincidence identifying function 442. For example, the image reconstructing function 444 is configured to carry out the reconstructing process using a Maximum Likelihood-Expectation Maximization (ML-EM) method pr an Ordered Subset-Expectation Maximization (OS-EM) method obtained by increasing the speed of the ML-EM method.

The scan controlling function 445 is configured to acquire nuclear medicine data by scanning the patient P by employing the PET gantry apparatus 10. The scan controlling function 445 is an example of an acquiring unit. The nuclear medicine data is data acquired by scanning the patient P by employing the PET gantry apparatus 10. For example, the nuclear medicine data may be single list mode data or may be list mode data.

More specifically, the scan controlling function 445 is configured to control the scan performed on the patient P by the PET gantry apparatus 10. For example, the scan controlling function 445 is configured to control the scan performed on the patient P by implementing the step-and-shoot scheme. According to the step-and-shoot scheme, the scan controlling function 445 is configured to scan the patient P, by alternately performing the acquisition of the nuclear medicine data in a different one of various bed positions and a bed position changing process to move the tabletop 33. The bed positions are acquisition positions being the positions in which the patient P is scanned. Further, the scan controlling function 445 is configured to scan the patient P in each of the bed positions for an acquisition period determined in advance. For example, the acquisition period may be 2 minutes.

Figure 2:
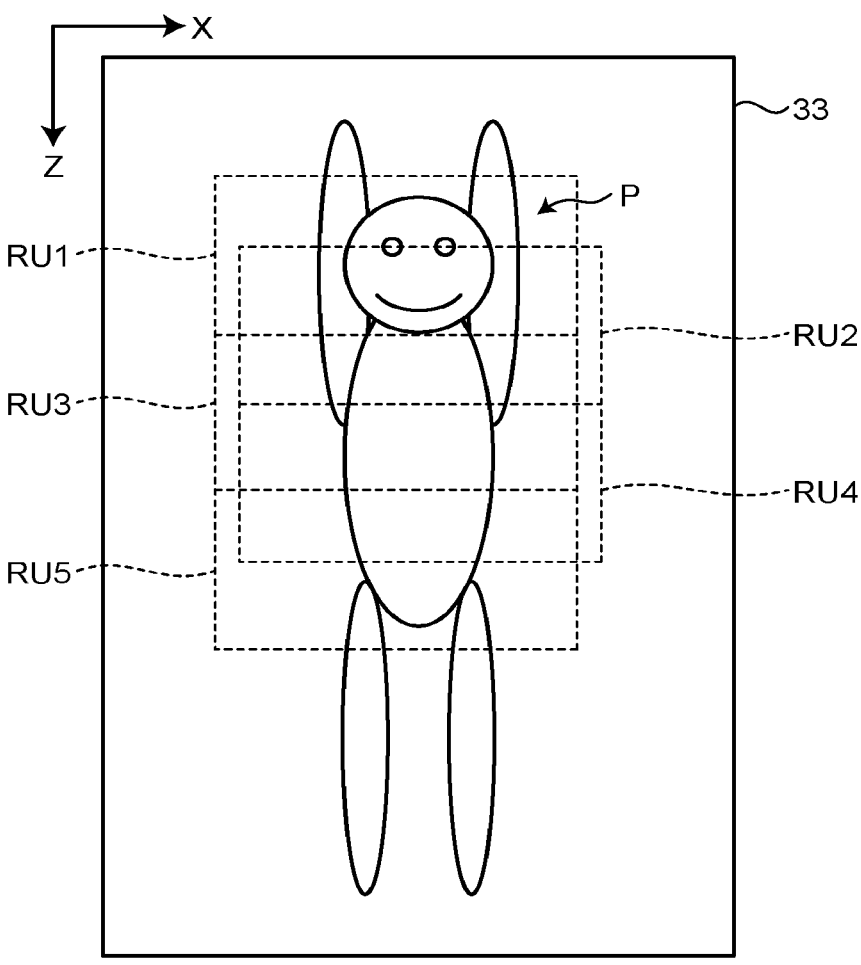
FIG. 2 is a drawing illustrating an example of a method for scanning an examined subject by using a step-and-shoot scheme.

FIG. 2 is a drawing illustrating an example of a method for scanning the patient P by using the step-and-shoot scheme. As illustrated in FIG. 2, the scan controlling function 445 is configured to scan the patient P in a first bed position over a first unit acquisition region RU1 for an acquisition period. When the scan of the first unit acquisition region RU1 is finished, the scan controlling function 445 is configured to move the tabletop 33 to a second bed position. After that, the scan controlling function 445 is configured, to scan the patient P in the second bed position over a second unit acquisition region RU2 for an acquisition period. Although FIG. 2 illustrates an example in which an overlap ratio between the first unit acquisition region RU1 and the second unit acquisition region RU2 is 50%, the overlap ratio is arbitrary. Further, the first unit acquisition region RU1 and the second unit acquisition region RU2 are out of alignment in the X-axis direction for explanation purposes only and do not necessarily need to be out of alignment in the X-axis direction in actuality. Further, the scan controlling function 445 is configured to repeatedly perform the acquisition and the moving of the tabletop 33, until the scan of a fifth unit acquisition region RU5 is finished in a fifth bed position.

The scan operating function 446 is configured to receive the operations performed on the scan by the scan controlling function 445. The scan operating function 446 is configured to receive the operations on the scan in a scan operation image G1.

Figure 3:
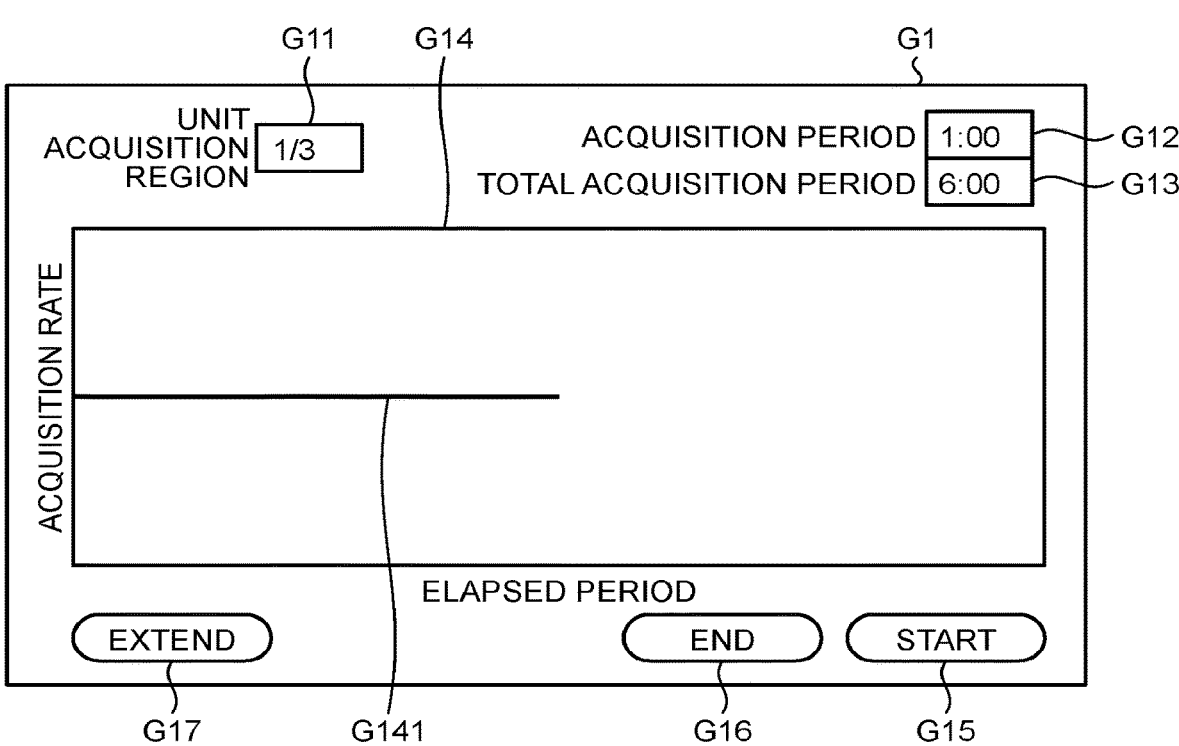
FIG. 3 is a drawing illustrating an example of a scan operation image.

FIG. 3 is a drawing illustrating an example of the scan operation image G1. The scan operation image G1 includes a unit acquisition region display region G11, an acquisition period display region G12, a total acquisition period display region G13, a scan status display region G14, a start button G15, an end button G16, and an extension button G17.

The unit acquisition region display region G11 is a region for displaying a unit acquisition region currently being acquired. The unit acquisition region display region G11 in FIG. 3 indicates that the acquisition is performed on the first one of the three unit acquisition regions. The acquisition period display region G12 is a region for displaying an elapsed period of the acquisition in the unit acquisition region. The acquisition period display region G12 in FIG. 3 indicates that the acquisition has been performed for 1 minute. The total acquisition period display region G13 is a region for displaying a total acquisition period from all the unit acquisition regions. The total acquisition period display region G13 in FIG. 3 indicates that there are three unit acquisition regions, and because the acquisition period of each of the unit acquisition regions is 2 minutes, the total acquisition period is 6 minutes.

The scan status display region G14 is a region for displaying an acquisition status of the count information. In the scan status display region G14, the vertical axis expresses the number of times of count information acquisition per unit period, whereas the vertical axis expresses an elapsed period of the acquisition in the unit acquisition region. Further, the scan operating function 446 is configured to display a line G141 indicating the number of times of acquisition and the elapsed period in the scan status display region G14.

The start button G15 receives an operation to instruct the scan controlling function 445 to start a scan. The end button G16 receives an operation to instruct the scan controlling function 445 to end the scan.

The extension button G17 receives an operation to extend the acquisition period of the unit acquisition region currently being acquired. For example, every time the extension button G17 is pressed once, the acquisition period is extended by a set time length that is set in advance. In other words, the scan operating function 446 is configured to receive, from the user, the input for extending the acquisition period. The scan operating function 446 is an example of a receiving unit. For example, the set time length is 10 seconds. For example, when the extension button G17 is pressed once while the first one of the six unit acquisition regions is being acquired, the PET-CT apparatus 1 is configured to extend the acquisition period of the first unit acquisition region by 10 seconds.

In this situation, if the patient P moves during the acquisition, the position of the patient P in the count information changes. For this reason, a PET image using both the count information before and the count information after the movement of the patient P would be unclear. In contrast, if a PET image was obtained by using the count information after the body movement, without using the count information before the body movement, the data statistic amount would be insufficient because the count information before the body movement is missing, and the image quality would be degraded.

To cope with this situation, upon discovering that the patient P moved, the user presses the extension button G17 in accordance with the elapsed period. For example, if the patient P moved when 1 minute has elapsed, the user presses the extension button G17 six times. As a result, the acquisition period of the unit acquisition region currently being acquired is extended by 60 seconds. With this configuration, the PET-CT apparatus 1 is able to acquire the count information after the movement of the patient P, for the acquisition period that was set in advance.

Further, factors for which the extension button G17 is pressed are not limited to the movement of the patient P. For example, for medical examinations such as a rubidium heart test, the user administers a drug such as a contrast agent for the patient P, after pressing the start button G15. Subsequently, the PET-CT apparatus 1 is configured to perform a scan on the patient P for whom the drug such as the contrast agent was administered, for an acquisition period set in advance.

However, in the situation where the drug administration is significantly delayed due to a trouble in a catheter insertion step, a malfunction of a drug dispenser, or the like, it would not be possible to complete the acquisition of the count information within the acquisition period set in advance. In that situation, the user presses the extension button G17 in accordance with the delay period. With this configuration, because the acquisition period is extended, the PET-CT apparatus 1 is able to performs the acquisition for the acquisition period expected in advance.

Further, besides via the extension button G17, the scan operating function 446 may receive an operation to extend the acquisition period of the unit acquisition region, via the input interface circuitry 43. For example, the scan operating function 446 may receive the operation to extend the acquisition period of the unit acquisition region, from a button formed using hardware.

The timing specifying function 447 is configured to specify timing of the body movement of the patient P during the acquisition of the nuclear medicine data. The timing specifying function 447 is an example of a specifying unit. Further, when the timing of the body movement of the patient P has been specified, the PET-CT apparatus 1 is configured to extend the acquisition period. More specifically, the timing specifying function 447 is configured to specify the timing of the body movement of the patient P, as extension timing satisfying an extension condition for extending the acquisition period. In this situation, the timing of the body movement of the patient P denotes the timing at which the body movement of the patient P is recognized. For example, the timing of the body movement of the patient P may be the timing at which the extension button G17 is pressed. For example, the timing specifying function 447 is configured to specify the timing at which the extension button G17 is pressed to be received by the scan operating function 446, as the extension timing.

The acquisition period setting function 448 is configured to set the acquisition period for acquiring the count information. Further, the scan controlling function 445 is configured to scan the patient P for the acquisition period set by the acquisition period setting function 448. More specifically, the acquisition period setting function 448 is configured to set the acquisition period with the unit acquisition region, before the patient P is scanned. In other words, the acquisition period setting function 448 is configured to set an initial value of the acquisition period, before the patient P is scanned.

Furthermore, the acquisition period setting function 448 is configured to extend the acquisition period of the scan, on the basis of the extension timing specified by the timing specifying function 447. The acquisition period setting function 448 is an example of a controlling unit. More specifically, when the timing specifying function 447 specifies the extension timing, the acquisition period setting function 448 is configured to extend the acquisition period of the unit acquisition region being acquired at the time of the extension timing being specified. In other words, when the acquisition of the nuclear medicine data and the bed position changing process are alternately performed according to the step-and-shoot scheme, the scan controlling function 445 is configured to extend the acquisition period of each of the bed positions. For example, the scan controlling function 445 is configured to extend the acquisition period of the scan, on the basis of the input of the pressing of the extension button G17 received by the scan operating function 446. In other words, the acquisition period setting function 448 is configured to extend the acquisition period by a time length corresponding to the number of times the extension timing has been specified. For example, when the extension timing has been specified six times, the acquisition period setting function 448 is configured to extend the acquisition period by 60 seconds.

The reconstruction designating function 449 is configured to receive an input of designating, from among the nuclear medicine data acquired during the acquisition period, certain nuclear medicine data to be used in a reconstructing process. The reconstruction designating function 449 is an example of an input unit. For example, the reconstruction designating function 449 is configured to receive the input of designating the certain nuclear medicine data to be used in the reconstructing process, within a reconstruction target designation image G2.

Figure 4:
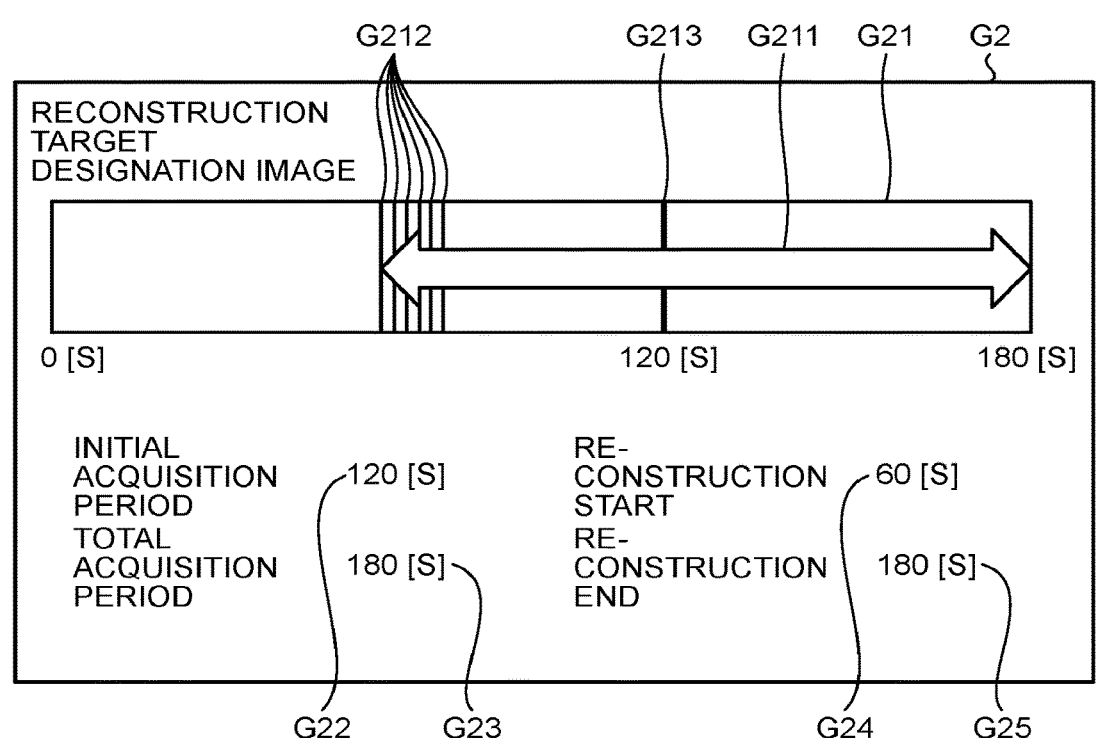
FIG. 4 is a drawing illustrating an example of a reconstruction target designation image.

FIG. 4 is a drawing illustrating an example of the reconstruction target designation image G2. The reconstruction target designation image G2 includes a designating bar G21, an initial acquisition period display region G22, a total acquisition period display region G23, a reconstruction start time display region G24, and a reconstruction end time display region G25. In the reconstruction target designation image G2 indicating the times during the acquisition period at which the extension timing was specified by the acquisition period setting function 448, the reconstruction designating function 449 is configured to receive the input of designating the target to be used in the reconstructing process.

The designating bar G21 is an image for designating certain count information to be used in the reconstructing process, from among the count information acquired in the unit acquisition region. The user designates the certain count information to be used in the reconstructing process, by designating a start point and an end point of the designating bar G21.

The designating bar G21 includes an acquisition target specifying image G211, an extension timing image G212, and an initial acquisition period image G213. The acquisition target specifying image G211 is an image for specifying the certain count information to be used in the reconstructing process, from among the count information acquired in the unit acquisition region. The PET-CT apparatus 1 is configured to use, in the reconstructing process, the count information in the range specified within the acquisition target specifying image G211.

The extension timing image G212 is an image indicating the times at which the extension timing was specified by the acquisition period setting function 448. The extension timing image G212 illustrated in FIG. 4 indicates that the extension timing was specified six times. The extension timing image G212 does not need to be indicated with solid lines and may be indicated with broken lines or in a different color or may use an image in other forms. The initial acquisition period image G213 indicates the acquisition period of the unit acquisition region that was set before the acquisition period was extended. In other words, the initial acquisition period image G213 indicates the initial value of the acquisition period.

The initial acquisition period display region G22 is a region for displaying the acquisition period of the unit acquisition region that was set before the acquisition period was extended. In other words, the initial acquisition period image G213 represents a region for displaying the initial value of the acquisition period. The total acquisition period display region G23 is a region for displaying the period required by the acquisition of the unit acquisition region. In other words, when the acquisition period has been extended, the total acquisition period display region G23 displays the acquisition period after the extension. Further, when the acquisition period has not been extended, the total acquisition period display region G23 displays the initial value of the acquisition period.

The reconstruction start time display region G24 is a region for displaying start timing of the acquisition of the certain count information to be used in the reconstructing process among the count information acquired in the unit acquisition region. The reconstruction end time display region G25 is a region for displaying end timing of the acquisition of the certain count information to be used in the reconstructing process among the count information acquired in the unit acquisition region.

Next, processes performed by the PET-CT apparatus 1 will be explained.

Figure 5:
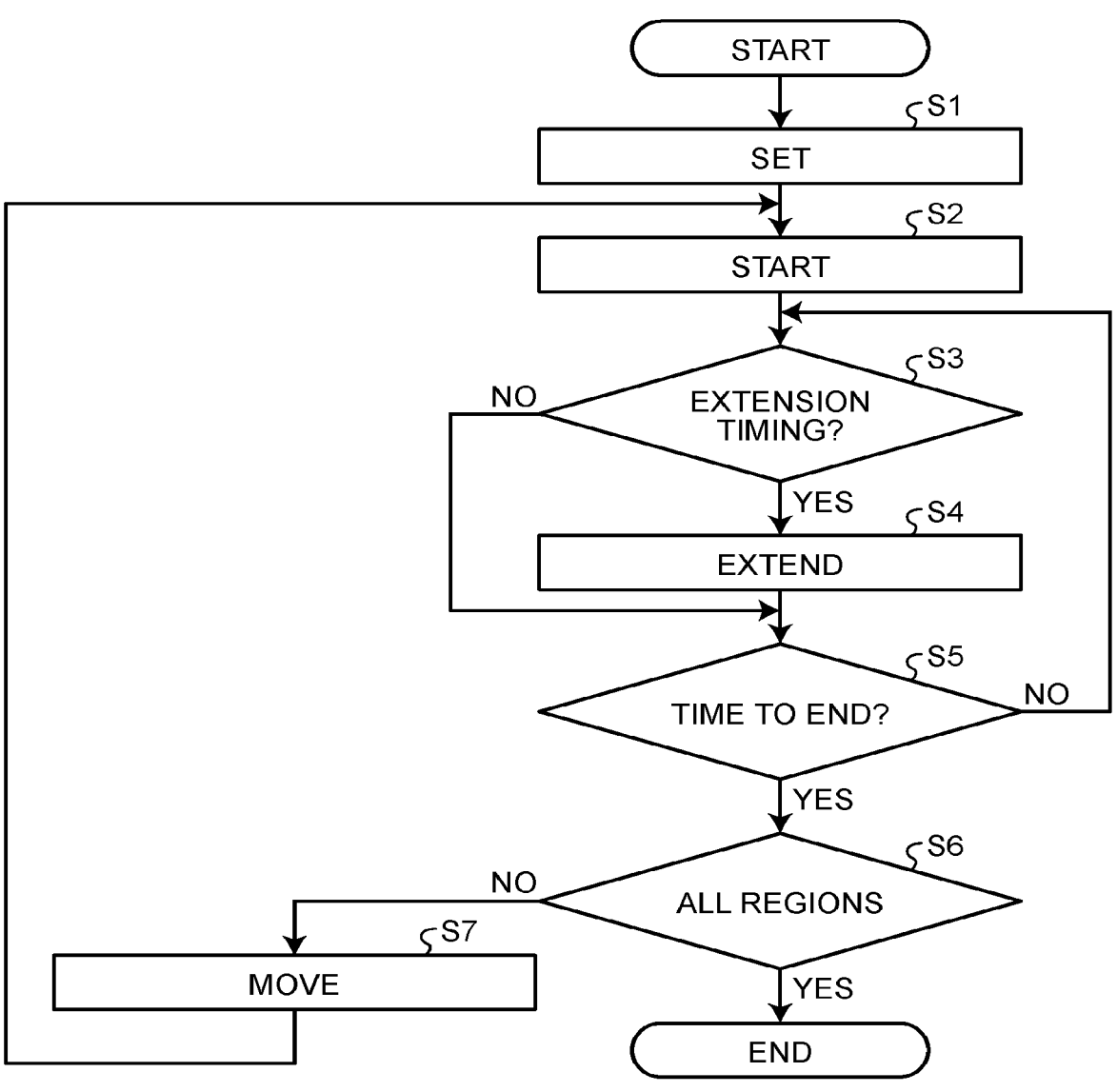
FIG. 5 is a flowchart illustrating an example of a scan process performed by the PET-CT apparatus according to the present embodiment.

FIG. 5 is a flowchart illustrating an example of a scan process performed by the PET-CT apparatus 1 according to the present embodiment.

The acquisition period setting function 448 sets an acquisition period of each of the unit acquisition regions (step S1).

The scan controlling function 445 starts a scan (step S2).

The timing specifying function 447 judges whether or not extension timing is specified (step S3). When extension timing is specified (step S3: Yes), the acquisition period setting function 448 extends the acquisition period of the scan on the basis of the extension timing (step S4).

When no extension timing is specified (step S3: No), the scan controlling function 445 judges whether or not the time to end the scan of the unit acquisition region has arrived (step S5).

When the time to end the scan of the unit acquisition region has not arrived (step S5: No), the timing specifying function 447 returns to step S3.

When the time to end the scan of the unit acquisition region has arrived (step S5: Yes), the scan controlling function 445 judges whether or not all the unit acquisition regions have been scanned (step S6).

When all the unit acquisition regions have not been scanned (step S6: No), the scan controlling function 445 moves to the next unit acquisition region to be scanned (step S7).

When all the unit acquisition region have been scanned (step S6: Yes), the PET-CT apparatus 1 ends the scan process.

As explained above, the PET-CT apparatus 1 according to the present embodiment is configured to acquire the nuclear medicine data by scanning the patient P. Further, the PET-CT apparatus 1 is configured to specify the extension timing including the pressing of the extension button G17 indicating that the patient P had a body movement during the acquisition of the nuclear medicine data. Further, on the basis of the extension timing, the PET-CT apparatus 1 extends the acquisition period of the scan for the patient P. Accordingly, the PET-CT apparatus 1 is able to extend the acquisition period.

First Modification Example

Besides the pressing of the extension button G17, the timing specifying function 447 may be configured to specify other events as extension timing. For example, the PET-CT apparatus 1 may include a detecting unit configured to detect a body movement of the patient P. The timing specifying function 447 may specify the extension timing on the basis of the detection of the body movement of the patient P by the detecting unit. The detecting unit may be a function configured to detect the body movement of the patient P from an image taken by a camera imaging the patient P, may be a weight sensor configured to detect the body movement of the patient P, or may be an infrared ray sensor configured to detect the body movement of the patient P. For example, the timing specifying function 447 may be configured to specify, as the extension timing, the detection of the body movement of the patient P from the image taken by the camera imaging the patient P. In another example, the timing specifying function 447 may be configured to specify, as the extension timing, the detection of the body movement of the patient P by the weight sensor or the infrared ray sensor configured to detect the body movement of the patient P.

Second Modification Example

Besides the pressing of the extension button G17, the timing specifying function 447 may be configured to specify other events as extension timing. The timing specifying function 447 may be configured to specify the extension timing on the basis of nuclear medicine data. In that situation, the nuclear medicine data may be single list mode data, may be list mode data, or may be a PET image resulting from a short scan and being reconstructed. For example, the timing specifying function 447 may be configured to specify the extension timing on the basis of a movement of the center of gravity of the patient P included in the nuclear medicine data. In another example, the timing specifying function 447 may be configured to specify the extension timing, by comparing a feature value in the nuclear medicine data at the time of the start of a scan extracted by an auto-encoder, with a feature value in the nuclear medicine data of a detection target extracted by the auto-encoder.

Third Modification Example

In the description above, the PET-CT apparatus 1 is configured to scan the patient P in the unit acquisition regions, by moving the tabletop 33 according to the step-and-shoot scheme, so that the timing specifying function 447 extends the acquisition period of the one or more unit acquisition regions. However, the PET-CT apparatus 1 may be configured to use a continuous table moving scheme by which the whole body of the patient P is scanned while the tabletop 33 is moved. In that situation, the timing specifying function 447 is configured to add the time period required to scan the patient P first in one direction and then in the opposite direction, or the time period required to scan the patient P in one direction, then in the opposite direction, and in the one direction again.

According to at least one aspect of the embodiments and the like described above, it is possible to extend the acquisition period.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A nuclear medicine diagnosis apparatus, comprising:
processing circuitry configured to:
 acquire nuclear medicine data by alternately performing scanning of one unit acquisition region of an examined subject at an acquisition position and changing of the acquisition position to another acquisition position to scan another unit acquisition region of the examined subject;
 determine whether a timing of a body movement of the examined subject is specified during the acquisition of the nuclear medicine data;
 when determining that the timing is specified, extend an acquisition period for scanning a particular unit acquisition region that is being scanned at the specified timing; and
 receive an input designating, from among the nuclear medicine data acquired during the extended acquisition period, nuclear medicine data to be used in a reconstructing process, the input being received through a reconstruction target designation image, in which an extension timing image indicating the specified timing of the body movement overlaps a bar image indicating the extended acquisition period of the acquired nuclear medicine data.

2. The nuclear medicine diagnosis apparatus according to claim 1, further comprising a sensor configured to detect the body movement of the examined subject,
 wherein the processing circuitry is further configured to specify the timing based on the detection of the body movement by the sensor.

3. The nuclear medicine diagnosis apparatus according to claim 1, wherein the processing circuitry is further configured to specify the timing based on the acquired nuclear medicine data.

4. The nuclear medicine diagnosis apparatus according to claim 1, wherein the processing circuitry is further configured to, when an input is received from a user, to extend the acquisition period of the scan based on the received input.

5. The nuclear medicine diagnosis apparatus according to claim 4, wherein the processing circuitry is further configured to extend the acquisition period by a time length corresponding to how many times the input has been received.

6. An acquisition period extending method, comprising:
acquiring nuclear medicine data by alternately performing scanning of one unit acquisition region of an examined subject at an acquisition position and changing of the acquisition position to another acquisition position to scan another unit acquisition region of the examined subject;
determining whether a timing of a body movement of the examined subject is specified during the acquisition of the nuclear medicine data;
when determining that the timing is specified, extending the acquisition period for scanning a particular unit acquisition region that is being scanned at the specified timing; and
receiving an input designating, from among the nuclear medicine data acquired during the extended acquisition period, nuclear medicine data to be used in a reconstructing process, the input being received through a reconstruction target designation image, in which an extension timing image indicating the specified timing of the body movement overlaps a bar image indicating the extended acquisition period of the acquired nuclear medicine data.

7. A non-transitory computer-readable medium including instructions that cause a computer to execute:

acquiring nuclear medicine data by scanning an examined subject by alternately performing scanning of one unit acquisition region of an examined subject at an acquisition position and changing of the acquisition position to another acquisition position to scan another unit acquisition region of the examined subject;

determining whether a timing of a body movement of the examined subject during the acquisition of the nuclear medicine data;

when determining that the timing is specified, extending an acquisition period for scanning a particular unit acquisition region that is being scanned at the specified timing; and receiving an input designating, from among the nuclear medicine data acquired during the extended acquisition period, nuclear medicine data to be used in a reconstructing process, the input being received through a reconstruction target designation image, in which an extension timing image indicating the specified timing of the body movement overlaps a bar image indicating the extended acquisition period of the acquired nuclear medicine data.

\* \* \* \* \*